United States Patent [19]
Camden

[11] Patent Number: 5,872,142
[45] Date of Patent: Feb. 16, 1999

[54] PHARMACEUTICAL COMPOSITIONS FOR INHIBITING THE GROWTH OF CANCERS

[75] Inventor: James Berger Camden, West Chester, Ohio

[73] Assignee: The Procter & Gamble Company, Cincinnati, Ohio

[21] Appl. No.: 792,741

[22] Filed: Feb. 3, 1997

Related U.S. Application Data

[62] Division of Ser. No. 473,819, Jun. 7, 1995, Pat. No. 5,770,616.

[51] Int. Cl.$^6$ .................................................. A61K 31/41
[52] U.S. Cl. ................................................. 519/383
[58] Field of Search .............................................. 514/383

[56] References Cited

U.S. PATENT DOCUMENTS

| | | | |
|---|---|---|---|
| 4,079,062 | 3/1978 | Van Reet et al. | 260/8 |
| 4,160,838 | 7/1979 | Van Reet et al. | 424/269 |
| 4,404,216 | 9/1983 | Richardson | 514/383 |
| 4,490,540 | 12/1984 | Heeres | 548/336 |
| 5,126,359 | 6/1992 | Stroech et al. | 514/383 |
| 5,144,951 | 9/1992 | King | 514/290 |
| 5,211,736 | 5/1993 | Lai | 504/275 |
| 5,360,612 | 11/1994 | Fries et al. | 514/383 |
| 5,565,478 | 10/1996 | Kohn et al. | 514/359 |
| 5,665,751 | 9/1997 | Camden | 514/383 |

FOREIGN PATENT DOCUMENTS

| | | |
|---|---|---|
| 1004029 | 9/1992 | Belgium . |
| 44605 | 1/1982 | European Pat. Off. . |
| 196 855 A | 10/1986 | European Pat. Off. . |
| 2078719 | 1/1982 | United Kingdom . |
| WO96/40119 | 12/1996 | WIPO . |

OTHER PUBLICATIONS

Physicians Desk Reference, 15:35:33, Diflucan, Medical Economics Data Production Co, Montvale, NJ (1995).
Benzaquen et al, Nature Medicine, 1, (6), Jun. 1995.
Schwartz et al. "Inhibition of all trans–retinoic acid metabolism by Fluconazole in vitro and in Patients with Acute Promyelocytic Leukemia", Biochem. Pharmacol., vol. 50, No. 7, pp. 923–928, (Sep. 1995).

*Primary Examiner*—Jerome D. Goldberg
*Attorney, Agent, or Firm*—Rose Ann Dabek; J. C. Rasser

[57] ABSTRACT

A pharmaceutical composition that inhibits the growth of tumors and cancers in mammals that comprises a material is disclosed. The particular material used is a 1H-1,2,4-triazole derivative. These compounds can also be used to treat viral infections.

16 Claims, No Drawings

PHARMACEUTICAL COMPOSITIONS FOR INHIBITING THE GROWTH OF CANCERS

This is a division of application Ser. No. 08/473,819, filed on Jun. 7, 1995 now U.S. Pat. No. 5,770,616.

TECHNICAL FIELD

This invention is a pharmaceutical composition that inhibits the growth of cancers, leukemia and tumors in mammals, particularly in human and warm blooded animals. The composition contains a 1H-1,2,4-triazole derivative. The compositions can also be used to treat viral infections.

BACKGROUND OF THE INVENTION

Cancers are the leading cause of death in animals and humans. The exact cause of cancer is not known, but links between certain activities such as smoking or exposure to carcinogens and the incidence of certain types of cancers and tumors has been shown by a number of researchers.

Many types of chemotherapeutic agents have been shown to be effective against cancers and tumor cells, but not all types of cancers and tumors respond to these agents. Unfortunately, many of these agents also destroy normal cells. The exact mechanism for the action of these chemotherapeutic agents are not always known.

Despite advances in the field of cancer treatment the leading therapies to date are surgery, radiation and chemotherapy. Chemotherapeutic approaches are said to fight cancers that are metastasized or ones that are particularly aggressive. Such cytocidal or cytostatic agents work best on cancers with large growth factors, i.e., ones whose cells are rapidly dividing. To date, hormones, in particular estrogen, progesterone and testosterone, and some antibiotics produced by a variety of microbes, alkylating agents, and anti-metabolites form the bulk of therapies available to oncologists. Ideally cytotoxic agents that have specificity for cancer and tumor cells while not affecting normal cells would be extremely desirable. Unfortunately, none have been found and instead agents which target especially rapidly dividing cells (both tumor and normal) have been used.

Clearly, the development of materials that would target tumor cells due to some unique specificity for them would be a breakthrough. Alternatively, materials that were cytotoxic to tumor cells while exerting mild effects on normal cells would be desirable. Therefore, it is an object of this invention to provide a pharmaceutical composition that is effective in inhibiting the growth of tumors and cancers in mammals with mild or no effects on normal cells.

More specifically, it is an object of this invention to provide an anti-cancer composition comprising a pharmaceutical carrier and a 1H-1,2,4-triazole derivative as defined herein along with a method for treating such cancers.

These and other objects will become evident from the following detailed description of this inventions.

SUMMARY OF THE INVENTION

A pharmaceutical composition for treatment of mammals, and in particular, warm blooded animals and humans, comprising a pharmaceutical carrier and an effective amount anti-cancer compound selected from the group consisting of:

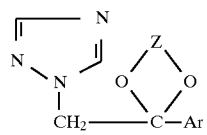

wherein Z is an alkylene selected from the group consisting of $CH_2$—$CH_2$—, —$CH_2$—$CH_2$—$CH_2$—, —$CH(CH_3)$—$CH(CH_3)$— and —$CH_2$—CH(alkyl) wherein said alkyl has from 1 to about 10 carbon atoms; and Ar is a member selected from the group consisting of phenyl, substituted phenyl, thienyl, halothienyl, naphthyl and fluorenyl, wherein "substituted phenyl" has the meaning of a phenyl radical having thereon from 1 to 3 substituents selected independently from the group consisting of halo, lower alkyl, lower alkyloxy, cyano and nitro. The therapeutically active acid addition salts of the foregoing compound (I) are also embraced within the scope of this invention.

As used in the foregoing definition of Z, the term "alkyl" is meant to include straight and branch chained hydrocarbon radicals having from 1 to about 10 carbon atoms, such as, for example, methyl, ethyl, 1-methylethyl, propyl, 1,1-dimethylethyl, butyl, pentyl, hexyl, heptyl, octyl, decyl and the like; as used herein "lower alkyl" may be straight or branch chained saturated hydrocarbons having from 1 to 6 carbon atoms, such as, for example, methyl, ethyl, propyl, 1-methylethyl, butyl, 1,1-dimethylethyl, pentyl, hexyl and the like alkyls; and the term "halo" is generic to halogen atoms of atomic weight less than 127; i.e., fluoro, chloro, bromo and iodo.

These compositions can be used to inhibit the growth of cancers and other tumors in humans or animals by administration of an effective amount either orally, rectally, topically or parenterally, intravenously or by injection into the tumor. These compositions do not significantly affect healthy cells as compared to adriamycin which has a detrimental effect on healthy cells.

These compositions are also be used to treat viruses.

DETAILED DESCRIPTION OF THE INVENTION

A. Definitions

As used herein, the term "comprising" means various components can be conjointly employed in the pharmaceutical composition of this invention. Accordingly, the terms "consisting essentially of" and "consisting of" are embodied in the term comprising.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The is specific "safe and effective amount" will, obviously, vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, a "pharmaceutical addition salts" is salt of the anti-cancer compound with an organic or inorganic acid.

These preferred acid addition salts are chlorides, bromides, sulfates, nitrates, phosphates, sulfonates, formates, tartrates, maleates, malates, citrates, benzoates, salicylates, ascorbates, and the like.

As used herein, a "pharmaceutical carrier" is a pharmaceutically acceptable solvent, suspending agent or vehicle for delivering the anti-cancer agent to the animal or human. The carrier may be liquid or solid and is selected with the planned manner of administration in mind.

As used herein, "cancer" refers to all types of cancers or neoplasm or malignant tumors and all types of cancers including leukemia that are found in mammals.

As used herein, the "anti-cancer compounds" are the 1H-1,2,4-triazoles and their salts. The exact 1H-1,2,4-triazoles are described in detail below. The preferred materials are the products sold under the names "propiconazole®" by Janssen Pharmaceutica NV (Belgium).

As used herein, "viruses" includes viruses which cause diseases (viral infections) in man and other warm blooded animals, such as HIV virus, herpes, influenza and rhinoviruses.

B. The Anti-Cancer Compounds

The anti-cancer compounds are 1H-1,2,4-triazole derivatives which are known for their antifungal activities. They are systemic materials used to prevent and eradicate fungi. The compounds have the following structure:

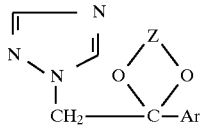

wherein Z is an alkylene selected from the group consisting of $CH_2$—$CH_2$—, —$CH_2$—$CH_2$—$CH_2$—, —$CH(CH_3)$—$CH(CH_3)$— and —$CH_2$—$CH(alkyl)$ wherein said alkyl has from 1 to about 10 carbon atoms; and Ar is a member selected from the group consisting of phenyl, substituted phenyl, thienyl, halothienyl, naphthyl and fluorenyl, wherein "substituted phenyl" has the meaning of a phenyl radical having thereon from 1 to 3 substituents selected independently from the group consisting of halo, lower alkyl, lower alkyloxy, cyano and nitro. The therapeutically active acid addition salts of the foregoing compound (I) are also embraced within the scope of this invention.

As used in the foregoing definition of Z, the term "alkyl" is meant to include straight and branch chained hydrocarbon radicals having from 1 to about 10 carbon atoms, such as, for example, methyl, ethyl, 1-methylethyl, propyl, 1,1-dimethylethyl, butyl, pentyl, hexyl, heptyl, octyl, decyl and the like; as used herein "lower alkyl" may be straight or branch chained saturated hydrocarbons having from 1 to 6 carbon atoms, such as, for example, methyl, ethyl, propyl, 1-methylethyl, butyl, 1,1-dimethylethyl, pentyl, hexyl and the like alkyls; and the term "halo" is generic to halogen atoms of atomic weight less than 127; i.e., fluoro, chloro, bromo and iodo. Their pharmaceutically acceptable acid addition salts with both organic and inorganic acids can also be used herein.

Preferred derivatives include: 1-[2-(2,4-dichlorophenyl)-1,3-dioxolan-2-ylmethyl]-1H-1,2,4-triazole; 1-[2-(2,4-dichlorophenyl)-4-methyl-1,3-dioxolan-2-ylmethyl]-1H-1,2,4-triazole, 1-[2-(2,4-dichlorophenyl)-4-ethyl-1,3-dioxolan-2-ylmethyl]-1H-1,2,4-triazole, 1-[2-(2,4-dichlorophenyl)-4-propyl-1,3-dioxolan-2-ylmethyl]-1H-1,2,4-triazole, 1-[2-(2,4-dichlorophenyl)-4-pentyl-1,3-dioxolan-2-ylmethyl]-1H-1,2,4-triazole, and the therapeutically active acid addition salts thereof.

These compounds are prepared according to the method described in U.S. Pat. No. 4,079,062 issued to Van Reet, et al, Mar. 14, 1978.

It is believed that these particular materials have the capability of reducing tumors or decreasing their growth significantly because of their ability to inhibit the synthesis of sterols.

C. Dosage

Any suitable dosage may be given in the method of the invention. The type of disease (cancer, leukemia or virus), the compound, the carrier and the amount will vary widely depending on the species of the warm blooded animal or human, body weight, and tumor being treated. Generally a dosage of between about 2 milligrams (mg) per kilogram (kg) of body weight and about 400 mg per kg of body weight is suitable. Preferably from 15 mg to about 150 mg/kg of body weight is used. Generally, the dosage in man is lower than for small warm blooded mammals such as mice. A dosage unit may comprise a single compound or mixtures thereof with other compounds or other cancer inhibiting compounds. The dosage unit can also comprise diluents, extenders, carriers and the like. The unit may be in solid or gel form such as pills, tablets, capsules and the like or in liquid form suitable for oral, rectal, topical, intravenous injection or parenteral administration or injection into or around the tumor.

D. Dosage Delivery Forms

The anti-cancer compounds are typically mixed with a pharmaceutically acceptable carrier. This carrier can be a solid or liquid and the type is generally chosen based on the type of administration being used. The active agent can be coadministered in the form of a tablet or capsule, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms would also include minerals and other materials to make them compatible with the type of injection or delivery system chosen.

Specific examples of pharmaceutical acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described in the following references: 7 *Modern Pharmaceutics,* Chapters 9 and 10 (Banker & Rhodes, Editors, 1979); Lieberman et al., *Pharmaceutical Dosage*

Forms: Tablets (1981); and Ansel, *Introduction to Pharmaceutical Dosage Forms 2nd Edition* (1976).

E. Method of Treatment

The method of treatment can be any suitable method which is effective in the treatment of the particular cancer type or virus that is being treated. Treatment may be oral, rectal, topical, parenteral or intravenous administration or by injection into the tumor and the like. The method of applying an effective amount also varies depending on the tumor being treated. It is believed that parenteral treatment by intravenous, subcutaneous, or intramuscular application of the 1H-1,2,4-triazole compounds, formulated with an appropriate carrier, additional cancer inhibiting compound or compounds or diluent to facilitate application will be the preferred method of administering the compounds to warm blooded animals.

The method of treating viral infections may also be by oral, rectal, topical, parenteral or intravenous administration.

In vitro Data

The following examples are illustrative and are not meant to be limiting to the invention.
Colon, Breast and Lung Tumor Cells Test The following cell culture tests were performed to test the toxicity of the N-phosphonoglycine compounds on colon, breast and lung human tumor cells. The viability of the cells were tested by looking at MTT (3-[4,5-dimethylthiazol-2-yl]-2,5-diphenyltetrazolium bromide) reduction. MTT assay is a well known measure of cell viability.

The colon tumor cells (HT29 from American Type Culture Collection (ATCC)) and the breast cells (MXI from cell lines from ATCC) were cultured in Eagle's Miminal Essential Medium with 10% fetal bovine serum. The lung tumor cells (A549 from ATCC cell lines) were cultured in Ham's F12 medium with 10% fetal bovine serum.

The tumor cells were passaged and seeded into culture flasks at the desired cell densities. The culture medium was decanted and the cell sheets were washed twice with phosphate buffered saline (PBS). The cells were trypsinized and triturated prior to seeding the flasks. Unless otherwise indicated the cultures were incubated at 37±1° C. in a humidified atmosphere of 5±1% carbon dioxide in air. The cultures were incubated until they were 50–80% confluent.

The cells were subcultured when the flasks were subconfluent. The medium was aspirated from the flasks and the cell sheets rinsed twice with PBS. Next, the Trypsin Solution was added to each flask to cover the cell sheet. The Trypsin Solution was removed after 30–60 seconds and the flasks were incubated at room temperature for two to six minutes. When 90% of the cells became dislodged, growth medium was added. The cells were removed by trituration and transferred to a sterile centrifuge tube. The concentration of cells in the suspension was determined, and an appropriate dilution was made to obtain a density of 5000 cells/ml. The cells were subcultured into the designated wells of the 96-well bioassay plates (200 microliter cell suspension per well). PBS was added to all the remaining wells to maintain humidity. The plates were then incubated overnight before test article treatment.

Each dose of test article was tested by treating quadruplicate wells of cultures with 100 microliter of each dilution. Those wells designated as solvent controls received an additional 100 microliter of methanol control; negative controls wells received an additional 100 microliters of treatment medium. PBS was added to the remaining wells not treated with test article or medium. The plates were then incubated for approximately 5 days.

At the end of the 5 day incubation, each dose group was examined microscopically to assess toxicity. A 0.5 mg/ml dilution of MTT was made in treatment medium, and the dilution was filtered through a 0,.45 micrometer filter to remove undissolved crystals. The medium was decanted from the wells of the bioassy plates. Immediately thereafter, 2000 microliter of the filtered MTT solution was added to all test wells except for the two untreated blank test wells. The two blank wells received 200 microliters of treatment medium. The plates were returned to the incubator for about 3 hours. After incubation, the MTT containing medium was decanted. Excess medium was added to each well and the plates were shaken at room temperature for about 2 hours.

The absorbance at 550 nm ($OD_{550}$) of each well was measured with a Molecular Devices (Menlo Park, Calif.) VMax plate reader.

The mean $OD_{550}$ of the solvent control wells and that of each test article dilution, and that of each of the blank wells and the positive control were calculated. The mean $OD_{550}$ of the blank wells was subtracted from the mean of the solvent control wells, and test article wells, respectively to give the corresponding mean $OD_{550}$ % of Control=corrected mean $OD_{550}$ of Test Article Dilution×100 corrected mean of $OD_{550}$ of Solvent Control Dose response curves were prepared as semi-log plots with % of control on the ordinate (linear) and the test article concentration on the abscissa (logarithmic). The $EC_{50}$ was interpolated from the plots for each test article.

For the test articles administered in methanol, separate responses were prepared to correct for the methanol data.

Adriamycin was used as a positive control. In all cases, it was more toxic than any of the test materials by one or two logs. Adriamycin is one of the more potent agents in current use and one with significant side effects. The peak plasma concentration of other, quite effective chemotherapeutic agents may be 10 to 50 times higher than that of Adriamycin. The EC-50 is the concentration at which one half the cells are killed.

TABLE I

| Test Material | EC-50 Result (ppml) | | |
| --- | --- | --- | --- |
| | HT29 | MX1 | A549 |
| Adriamycin | 0.00639 | 0.00078 | 0.00373 |
| Propiconazole | 0.0331 | 0.0284 | 0.113 |

These experiments show that these compositions are effective in killing tumor cells without significantly affecting healthy cells. They are safer than adriamycin.

What is claimed is:

1. A method of treating cancer susceptible to treatment in warm blooded mammals comprising administering to said mammals a safe and effective amount of a 1H-1,2,4-triazole derivative of the formula:

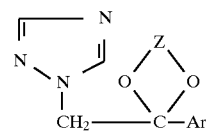

wherein Z is an alkylene selected from the group consisting of

CH$_2$—CH$_2$—, —CH$_2$—CH$_2$—CH$_2$—, —CH(CH$_3$)—CH(CH$_3$)— and —CH$_2$—CH(alkyl) wherein said alkyl has from 1 to about 10 carbon atoms; and Ar is a member selected from the group consisting of phenyl, substituted phenyl, thienyl, halothienyl, naphthyl and fluorenyl or therapeutically active acid addition salts thereof.

2. A method according to claim 1 wherein from about 2 mg/kg body weight to about 400 mg/kg of said 1H-1,2,4-triazole is administered per dose.

3. A method according to claim 2 wherein said 1H-1,2,4-triazole is administered orally or enterically, intravenously, peritoneally, parenterally or by injection into the tumor.

4. A method according to claim 3 wherein said 1H-1,2,4-triazole is selected from the group consisting of:

1-[2-(2,4-dichlorophenyl)-1,3-dioxolan-2-ylmethyl]-1H-1,2,4-triazole; 1-[2-(2,4-dichlorophenyl)-4-methyl-1,3-dioxolan-2-ylmethyl]-1H-1,2,4-triazole, 1-[2-(2,4-dichlorophenyl)-4-ethyl-1,3-dioxolan-2-ylmethyl]-1H-1,2,4-triazole, 1-[2-(2,4-dichlorophenyl)-4-propyl-1,3-dioxolan-2-ylmethyl]-1H-1,2,4-triazole, 1-[2-(2,4-dichlorophenyl)-4-pentyl-1,3-dioxolan-2-ylmethyl]-1H-1,2,4-triazole, and the therapeutically active acid addition salts thereof.

5. A method according to claim 4 wherein said therapeutically active acid addition salts are selected from the group consisting of chlorides, bromides, sulfates, nitrates, phosphates, sulfonates, formates, tartrates, maleates, malates, citrates, benzoates, salicylates, ascorbates and mixtures thereof.

6. A method according to claim 3 wherein said 1H-1,2,4-triazole is administered in a solid form.

7. A method according to claim 6 wherein said solid form includes a carrier selected from the group consisting of lactose, sucrose, gelatin and agar.

8. A method according to claim 7 wherein from about 15 mg/kg to about 150 mg/kg of said 1H-1,2,4-triazole is administered.

9. A method according to claim 8 wherein said 1H-1,2,4-triazole is administered in a liquid form.

10. A method according to claim 9 wherein said liquid dosage from is selected from the group consisting of aqueous solutions, alcohol solutions, emulsions, suspensions, and suspensions reconstituted from non-effervescent and effervescent preparations and suspensions in pharmaceutically acceptable fats or oils.

11. A method according to claim 10 wherein said liquid dosage from a member selected from the group consisting of suspending agents, diluents, sweeteners, flavorants, colorants, preservatives, emulsifying agents and coloring agents, and mixtures thereof.

12. A method of treating colon, breast and lung cancer in warm blooded mammals comprising administering to said mammals a safe and effective amount of a 1H-1,2,4-triazole derivative of the formula:

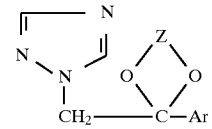

wherein Z is an alkylene selected from the group consisting of

CH$_2$—CH$_2$—, —CH$_2$—CH$_2$—CH$_2$—, —CH(CH$_3$)—CH(CH$_3$)— and —CH$_2$—CH(alkyl) wherein said alkyl has from 1 to about 10 carbon atoms; and Ar is a member selected from the group consisting of phenyl, substituted phenyl, thienyl, halothienyl, naphthyl and fluorenyl or therapeutically active acid addition salts thereof.

13. A method according to claim 12 wherein from about 2 mg/kg body weight to about 400 mg/kg of said 1H-1,2,4-triazole is administered per dose.

14. A method according to claim 12 wherein from about 150 mg to about 400 mg of said 1H-1,2,4-triazole is administered.

15. A method according to claim 12 wherein said 1H-1,2,4-triazole is administered in a solid form.

16. A method according to claim 12 wherein said 1H-1,2,4-triazole is in a liquid form and is selected from the group consisting of aqueous solutions, emulsions, suspension solutions, and suspensions reconstituted from non-effervescent and effervescent preparations.

* * * * *

UNITED STATES PATENT AND TRADEMARK OFFICE
CERTIFICATE OF CORRECTION

PATENT NO. : 5,872,142
DATED : February 16, 1999
INVENTOR(S) : James Berger Camden It is certified that error appears in the above-identified patent and that said Letters Patent is hereby corrected as shown below:

Column 5,
Line 27, delete "N-phosphonoglycine" and substitute --1H-1,2,4-triazole--, therefor.

In Claim 1,

Column 7,
Line 8; and in Claim 12, column 8, line 29; after 'fluorenyl', insert --;--.

In Claim 2, column 7, line 11; Claim 4, column 7, line 26; and Claim 16, column 8, line 39; delete "II" and substitute --H--, therefor.

In Claim 3,

Column 7,
Line 14, after 'orally', insert --,--.
Line 14, delete "or".

In Claim 9,

Column 7,
Line 42, delete "8" and substitute --3--, therefor.

In Claim 10,

Column 7,
Line 45, delete "dosage from", and substitute --form--, therefor.

Column 8,
Line 2, delete the first occurrence of "and".

UNITED STATES PATENT AND TRADEMARK OFFICE
CERTIFICATE OF CORRECTION

PATENT NO. : 5,872,142
DATED : February 16, 1999
INVENTOR(S) : James Berger Camden It is certified that error appears in the above-identified patent and that said Letters Patent is hereby corrected as shown below:

In Claim 10,

Column 8,
Line 2, delete the second occurrence of "and", and substitute --or--, therefor.

In Claim 11,

Column 8,
Line 6, delete "dosage from a member", and substitute --form is--, therefor.
Line 8, delete "and" and substitute --,--, therefor.

In Claim 12,

Column 8,
Line 10, delete "and" and substitute --or--, therefor.

In Claim 16,

Column 8,
Line 43, delete "and," and substitute --or--,therefor.

Signed and Sealed this

Nineteenth Day of June, 2001

*Attest:*

NICHOLAS P. GODICI
*Attesting Officer*  *Acting Director of the United States Patent and Trademark Office*